US011200967B1

(12) United States Patent
Jain (10) Patent No.: US 11,200,967 B1
(45) Date of Patent: Dec. 14, 2021

(54) MEDICAL PATIENT SYNERGISTIC TREATMENT APPLICATION

(71) Applicant: Sandeep Jain, Davie, FL (US)

(72) Inventor: Sandeep Jain, Davie, FL (US)

( * ) Notice: Subject to any disclaimer, the term of this patent is extended or adjusted under 35 U.S.C. 154(b) by 196 days.

(21) Appl. No.: 15/480,321

(22) Filed: Apr. 5, 2017

Related U.S. Application Data

(60) Provisional application No. 62/318,753, filed on Apr. 5, 2016.

(51) Int. Cl.
*G16H 10/60* (2018.01)

(52) U.S. Cl.
CPC .................................. *G16H 10/60* (2018.01)

(58) Field of Classification Search
CPC ......... G16H 10/60; G16H 50/20; G06F 19/34
USPC ....................................................... 705/2–3
See application file for complete search history.

(56) References Cited

U.S. PATENT DOCUMENTS

| 7,392,199 | B2 | 6/2008 | Karlov et al. |
| 7,725,565 | B2 | 5/2010 | Li et al. |
| 2008/0133275 | A1 | 6/2008 | Haug et al. |
| 2009/0024332 | A1* | 1/2009 | Karlov ............... G06Q 50/22 |
| | | | 702/19 |
| 2009/0172036 | A1* | 7/2009 | Marx .............. G06Q 10/06398 |
| 2012/0230557 | A1 | 9/2012 | Calman et al. |
| 2012/0245952 | A1 | 9/2012 | Halterman et al. |
| 2012/0277546 | A1* | 11/2012 | Soykan .............. A61B 5/0205 |
| | | | 600/301 |
| 2013/0047113 | A1 | 2/2013 | Hume et al. |
| 2013/0174073 | A1* | 7/2013 | Ash ..................... G16H 50/30 |
| | | | 715/771 |
| 2013/0226616 | A1 | 8/2013 | Nigam et al. |
| 2013/0231949 | A1* | 9/2013 | Baronov ............... G06Q 50/22 |
| | | | 705/2 |
| 2014/0122126 | A1 | 5/2014 | Riskin |
| 2014/0122389 | A1 | 5/2014 | Riskin |
| 2014/0142970 | A1 | 5/2014 | Baronov et al. |
| | | | (Continued) |

FOREIGN PATENT DOCUMENTS

WO    WO-2016094330 A2 *   6/2016    ............. G16B 40/00

OTHER PUBLICATIONS

Kathryn Laskey, "Sensitivity Analysis for Probability Assessments in Bayesian Networks," Jun. 1995, IEEE Transactions on Systems, Man, and Cybernetics vol. 25 No. 6 (Year: 1995).*

*Primary Examiner* — Jason S Tiedeman
*Assistant Examiner* — Rachel F Durnin
(74) *Attorney, Agent, or Firm* — Allen D Hertz, P. A.; Allen D. Hertz (57) ABSTRACT

An application operating on a portable computing device that generates a suggested hypothesis of at least one of: a diagnosis, a treatment, and subsequent medical investigation. The application receives quantified subfactors, collectively defining factors, for each patient. Subfactors of the medical condition are related to the history, symptoms, signs, tests, and responses to the treatment. The application determines an odds ratio for each factor regarding each hypothesized medical condition as well as an associated prevalence. The application can also determine a respective sensitivity and specificity. Posterior probability distribution, such as using Bayesian statistics, can be applied using odds ratios, prevalence, sensitivity specificity, and the associated correlations to determine the suggested hypothesis of the diagnosis, treatment, and any next tests.

20 Claims, 2 Drawing Sheets

(56) References Cited

U.S. PATENT DOCUMENTS

| | | | |
|---|---|---|---|
| 2014/0275807 A1 | 9/2014 | Redei | |
| 2014/0324469 A1 | 10/2014 | Reiner | |
| 2015/0019248 A1 | 1/2015 | Anand et al. | |
| 2015/0081323 A1 | 3/2015 | Jackson et al. | |
| 2015/0142704 A1 | 5/2015 | London | |
| 2015/0193583 A1* | 7/2015 | McNair | G16H 50/20 705/2 |
| 2015/0294088 A1 | 10/2015 | Walker et al. | |
| 2015/0317449 A1* | 11/2015 | Eder | G06Q 50/22 600/595 |
| 2015/0324527 A1 | 11/2015 | Siegel et al. | |
| 2015/0324548 A1 | 11/2015 | Eder | |
| 2015/0347704 A1 | 12/2015 | Baronov et al. | |
| 2016/0004298 A1 | 1/2016 | Mazed et al. | |
| 2016/0103960 A1 | 4/2016 | Hume et al. | |

* cited by examiner

FIG. 1

| # | Data Factor | Severity (a) | Quality (b) | Time Course (c) | Hypothesis A=CHF Odds Ratio | CHF Odds if Neg/NL | Hypothesis B=P Embolism Odds Ratio | P E Odds if Neg/NL |
|---|---|---|---|---|---|---|---|---|
| History | | | | | | | | |
| 1 | History of CHF | EF 25% | From MI | 10 yr ago | 4 | 0.5 | 0.5 | 2 |
| Symptoms | | | | | | | | |
| 2 | Orthopnea | Severe | Suffocating | Over 2 days | 3 | 0.7 | 1.5 | 1.5 |
| 2 | Hemoptysis | Small AMT (Teaspoon) | Bright Red | 1 day | 2 | 1 | 5 | 1 |
| 4 | Pleuritic Chest Pain | Sudden / Severe | Pinching | 1 day | 0.5 | 1.5 | 4 | 0.7 |
| Signs | | | | | | | | |
| 5 | S3 Gallop | Prominent | Soft | Unknown | 2 | 1 | 2 | 0.8 |
| 6 | JVD | 5 cm | Hepatojugular Refux | Unknown | 2 | 0.8 | 2 | 0.8 |
| 7 | Rales | Half Way | Fine | Unknown | 4 | 0.7 | 1.5 | 1 |
| Lab Test Result(s) | | | | | | | | |
| 8 | Troponin | Small Increase | Specific | New | 3 | 1 | 2 | 1 |
| 9 | BNP | Marked | Specific | New | 3 | 0.3 | 1.5 | 1 |
| 10 | D-Dimer | High | Non Specific | Unknown | 1.5 | 2 | 3 | 0.2 |
| Radiology Test Result(s) | | | | | | | | |
| 11 | CHF | Bat Wing Picture | Typical CHF | New from 10 day ago | 4 | 0.8 | 0.3 | 1.5 |
| 12 | DVT on LE US | Extensive | Acute | New | 0.3 | 0.6 | 3 | 1 |
| Response to Treatment | | | | | | | | |
| 13 | Improved P Lasix | 50% better | Definite | 2 hrs | 3 | 0.7 | 0.6 | 1.5 |

*Table: Example of Dataset*

*FIG. 2*

MEDICAL PATIENT SYNERGISTIC TREATMENT APPLICATION

CROSS-REFERENCE TO RELATED APPLICATION

This Non-Provisional Utility Patent application claims the benefit of U.S. Provisional Patent Application Ser. No. 62/318,753 filed on Apr. 5, 2016, which is incorporated herein in its entirety.

FIELD OF THE INVENTION

The present invention relates to an Application directed towards the patient treatment. More specifically, the present invention relates to an Application to aid both medical professionals and patients in optimizing the overall quality of care, including diagnosis, optimization of records, optimization towards diagnosis and proposed treatments, conferencing of medical professionals for obtaining a convergence of opinions, optimization of timing for acquisition and review of patient records, and the like.

FIELD OF THE INVENTION

The present invention relates to an Application directed towards the patient treatment. More specifically, the present invention relates to an Application to aid both medical professionals and patients in optimizing the overall quality of care, including diagnosis, optimization of records, optimization towards diagnosis and proposed treatments, conferencing of medical professionals for obtaining a convergence of opinions, optimization of timing for acquisition and review of patient records, and the like.

BACKGROUND OF THE INVENTION

Medical practice is fragmented, wherein the information is not structured between doctors for each patient. Electronic Medical Records (EMRs) are configured to satisfy arbitrary meaningful use goals set by centers for Medicare and Medicaid services, saddled with excess and distorted documentation for billing and legal purposes, hobbled by regulations and fragmented by multiple players that don't communicate, waste time for minimal benefit so far. Communication or lack thereof is one main reason for missed and/or incorrect diagnosis, hospital admission, readmission and duplication of care.

Communication and record keeping impacts the quality of treatment of patience. For example, a patient can inform a medical professional of signs and symptoms. Currently, the medical professional might record only a portion of the information provided by the patient. Additionally, the information documented may be interpreted differently between medical professionals.

Obtaining medical records for a patient can be time consuming. Particularly in a condition where the medical records are stored at different providers. For example, a portion of the patient's medical records may be stored at one medical provider a second portion may be stored at a second medical provider and the balance may be stored at a third medical provider or distributed to a number of medical providers. Correctly interpreting the patient's medical records can be difficult, as each medical professional may have their own terminology, such as terminology residing in proprietary electronic medical records (EMR's). Data sharing is further limited by barriers, such as access, cost, interface compatibility, Medical record keeping is increasingly time consuming. Government regulations, insurance company requirements, and other governing requirements dictate specific formats for documenting medical records for each patient. This requirement significantly increases time required for generating and storing the records.

Obtaining records from data collection devices, such as X-ray machines, CT-scanners, Magnetic Resonance Imaging machines (MRI), electrocardiogram (EKG or ECG), and the like can be tedious. The volume of medical records can be overwhelming to the user as well as any impact on a bandwidth of communication due to excessive data.

Several mobile healthcare messaging Applications are currently available. These Applications are generally Health Insurance Portability and Accountability Act (HIPAA) compliant text messaging processes among doctors.

Accordingly, there remains a need in the art for a system and associated method of use to improve communications between medical professionals, optimize data collection for analysis to diagnose and treat patients, unify collected data into a simpler, universally understandable format for consistent interpretation between medical professionals, broaden a scope of input for diagnosis and treatment of patients, track treatment of patients, and the like. Building an Application connecting the patient with their outpatient and inpatient doctors, their staff and all among themselves for intelligent communication has potential to improve healthcare in a big way and provides a huge opportunity.

BRIEF DESCRIPTION OF THE INVENTION

In accordance with one embodiment of the present invention, the invention consists of an application operating on a portable computing device, the application operating in accordance a method comprising steps of:
  accessing the portable computing device, the computing device comprising a microprocessor in digital communication with a digital data storage device;
  establishing and maintaining a database of a plurality of patients' electronic medical records;
  entering a series of subfactors into the portable computing device, wherein the subfactors are entered in a quantified format, collectively the subfactors define a factor;
  storing the series of quantified subfactors in a patient's electronic medical records;
  calculating an odds ratio based upon the factors associated with a health condition within the stored patient electronic medical records;
  calculating a prevalence based upon a frequency of previously determined diagnoses associated with other patients within the database of patient's electronic medical records; and
  determining a suggested hypothesis of at least one of a diagnosis and a treatment based upon the odds ratios of the factors associated with the health condition affecting multiple possible hypotheses of possible diagnosis and a possible treatment within the patient medical records, wherein the step of determining the hypothesis is accomplished by the microprocessor.

In a second aspect, the subfactors can include at least one of: severity scores, quality scores, time course scores and response to treatment scores.

In another aspect, the method further comprising steps of:
adjusting the quantified subfactors in a patient's electronic medical records to determine if the adjustment of the quantified subfactors affects the suggested hypothesis of at least one of a diagnosis and a treatment.

In yet another aspect, the method further comprising a step of:
adjusting the odds ratios based upon the factors associated with a health condition within the stored patient electronic medical records to determine if the adjustment of the odds ratios affects the suggested hypothesis of at least one of a diagnosis and a treatment.

In yet another aspect, the prevalence can be based upon at least one of: location, age, ethnicity, gender, genetic makeup, environmental exposures, family history, environmental clustering, geographic clustering, incidence of a given condition, incidence of a given condition in a geographic region, and recent patient travel history.

In yet another aspect, the method further comprising steps of:
entering a final diagnosis respective to the suggested hypothesis of at least one of a diagnosis and a treatment based upon the odds ratios and prevalence;
establishing a correlation between the final diagnosis and the suggested hypothesis of at least one of a diagnosis and a treatment based upon the odds ratios and prevalence,
using the correlation between the final diagnosis and the suggested hypothesis of at least one of a diagnosis and a treatment based upon the odds ratios to improve the step of determining the odds ratios and prevalence.

In yet another aspect, the factors can include at least one of: different types, symptoms, signs, lab tests, imaging tests, and response to treatment.

In yet another aspect, the method further comprising a step of:
employing correlations between at least one of a numerically characterization of the factors, a quantified characterization of the factors, and digitized detail of the factors respective to at least one of a severity, a quality, a time course, and an odds ratios of factors to calculate the probabilities for different hypothesis.

In accordance with a variant of the original embodiment of the present invention, the variant consists of an application operating on a portable computing device, the application operating in accordance a method comprising steps of:
accessing the portable computing device, the computing device comprising a microprocessor in digital communication with a digital data storage device;
establishing and maintaining a database of a plurality of patients' electronic medical records;
entering a series of subfactors into the portable computing device, wherein the subfactors are entered in a quantified format, collectively the subfactors define a factor;
storing the series of quantified subfactors in a patient's electronic medical records;
calculating an odds ratio based upon the factors associated with a health condition within the stored patient electronic medical records;
calculating a prevalence based upon a frequency of previously determined diagnoses associated with other patients within the database of patient's electronic medical records; and
determining a suggested hypothesis of at least one of a diagnosis and a treatment by forming a posterior probability distribution using the odds ratios of the factors associated with a health condition and the prevalence of the health conditions, wherein the step of determining the suggested hypothesis is accomplished by the microprocessor.

In yet another aspect, the step of forming the posterior probability distribution is accomplished using Bayesian statistics.

In yet another aspect, the method further comprising steps of:
entering a final diagnosis respective to the suggested hypothesis of at least one of a diagnosis and a treatment based upon the odds ratios and prevalence;
entering a final diagnosis respective to the suggested hypothesis of at least one of a diagnosis and a treatment based upon the odds ratios and prevalence;
establishing a correlation between the final diagnosis and the suggested hypothesis of at least one of a diagnosis and a treatment based upon the odds ratios and prevalence,
using the correlation between the final diagnosis and the suggested hypothesis of at least one of a diagnosis and a treatment based upon the odds ratios to improve the step of determining the odds ratios and prevalence.

A In yet another aspect, the posterior probability distribution calculates the likelihood of the observed distribution as a function of parameter values;
multiplies a likelihood function by the prior distribution, and
normalizes the likelihood function to obtain a unit probability over all possible values.

In yet another aspect, the posterior probability distribution is determined using Bayesian statistics, the method further comprising a step of:
including a respective sensitivity and specificity applied to the pretest probability in Bayesian statistics to obtain post test probabilities for at least one of a negative test and a positive test for each new test.

In yet another aspect, the subfactors can include at least one of: severity scores, quality scores, time course scores and response to treatment scores.

In yet another aspect, the method further comprising steps of:
adjusting the quantified subfactors in a patient's electronic medical records to determine if the adjustment of the quantified subfactors affects the suggested hypothesis of at least one of a diagnosis and a treatment.

In yet another aspect, the method further comprises a step of:
learning to increase accuracy of each subsequently suggested hypothesis of at least one of a diagnosis and a treatment by employing correlations with considerations which include at least one of: posterior probability distribution, subfactors, factors, odds ratios, prior prevalence of the health conditions, and collected data.

In yet another aspect, the method further comprises a step of:
applying at least one of Markov models and Monte Carlo simulations to further enhance the step of determining the hypothesis of at least one of a diagnosis and a treatment, wherein the at least one of Markov models and Monte Carlo simulations are accomplished by the microprocessor.

In accordance with a variant of the original embodiment of the present invention, the variant consists of an application operating on a portable computing device, the application operating in accordance a method comprising steps of:

accessing the portable computing device, the computing device comprising a microprocessor in digital communication with a digital data storage device;

establishing and maintaining a database of a plurality of patients' electronic medical records;

entering a series of subfactors into the portable computing device, wherein the subfactors are entered in a quantified format, collectively the subfactors define a factor;

storing the series of quantified subfactors in a patient's electronic medical records;

calculating an odds ratio based upon the factors associated with a health condition within the stored patient electronic medical records;

calculating a prevalence based upon a frequency of previously determined diagnoses associated with other patients within the database of patient's electronic medical records;

determining a suggested hypothesis of at least one of a diagnosis and a treatment based upon the odds ratios of the factors associated with the health condition affecting multiple possible hypothesis of possible diagnosis and a possible treatments within the patient medical records, wherein the step of determining the hypothesis is accomplished by the microprocessor; and determining a next medical investigation based upon a respective sensitivity and specificity wherein the step of determining the next medical investigation is accomplished by the microprocessor.

In yet another aspect, the method further comprises a step of.

determining a plurality of next medical investigations based upon a respective sensitivity and specificity.

In yet another aspect, the method further comprises a step of.

determining a plurality and order of next medical investigations based upon a respective sensitivity and specificity.

DETAILED DESCRIPTION OF THE INVENTION

Figure 1:
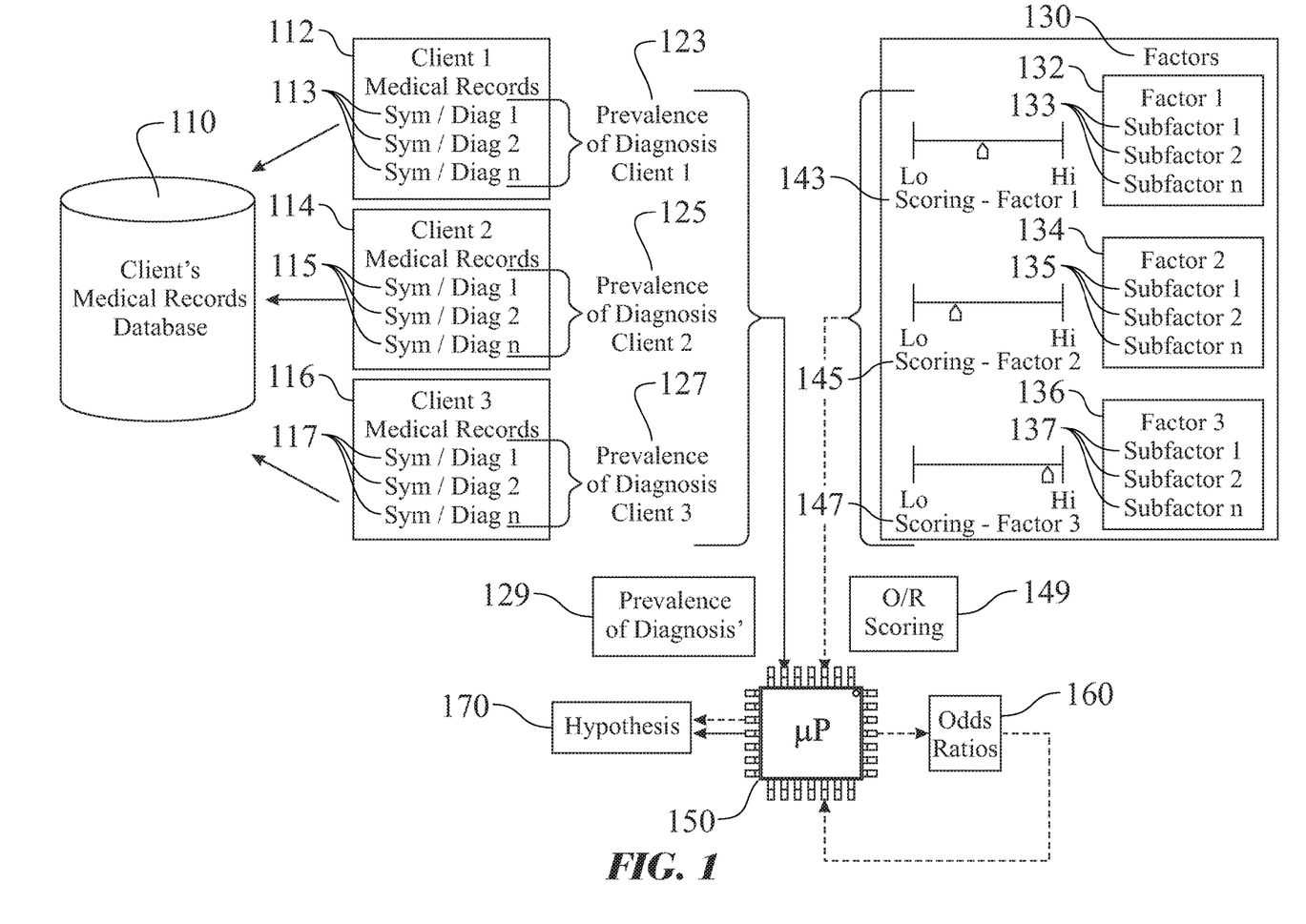
FIG. 1 presents an exemplary schematic detailing a process for determining one or more hypotheses of at least one of a diagnosis and a treatment.

The present invention overcomes the deficiencies of the known art by disclosing an Application providing improvements for medical treatment of a patient, providing a method for determining at least one hypothesis 170 of at least one of a diagnosis and a treatment, as illustrated in FIG. 1. More specifically, the Application obtains and manages patent demographic information, patient geographical information, patient medical data 110, converts medical data into a user specific dialect, acquires and collects medical records within a pre-established span of time prior to an appointment or an anticipated arrival time of a patient, enables collective analysis of the patient's medical records 112, 114, 116 by a team of medical professionals located in one or more locations, enables analysis simultaneously or over different times, enables optimization of analysis of the medical records 112, 114, 116 based upon previous experiences of the patient and/or other patients, and other advantages over the current state of the art. The Application can be patient concentric. The Application can be adapted to be patient authorized.

The present invention employs an Application adapted for use on a Smartphone or any other suitable portable computing device. The Application would be loaded onto devices operated by patients, the patient's family/health surrogate, the patient's doctors, the doctor's staff, medical facility employees caring for the patient, home health care providers, rehabilitation center employees, and any other suitable person.

The invention provides an Application and an associated support network; the Application providing assistance to the Medical profession and patients. The Application is adapted to run on a portable computing device, such as a portable computing tablet, a Smartphone, a laptop computer, and the like. The Application employs a wired or preferably wireless communication circuit for access to a network, such as a secured portion of the Internet. The communication circuit can utilize any suitable protocol, including Ethernet, Wi-Fi, Cellular communications, or any other suitable network communication protocol, or combination thereof. The Application would utilize the network to access remotely located central electronic storage devices serving various medical providers, such as physician's offices, medical specialist's offices, hospitals, emergency care centers, medical laboratories, pharmacies, diagnostic centers, insurance carriers, radiologist centers, rehabilitation centers, nursing centers, mental health care facilities, and any other suitable medical data source. Each facility would be in communication with a medical records data server 110, wherein the medical records data server would be accessible through the associated network. Each electronic device would include at least one electronic data storage media in signal communication with a microprocessor 150.

One aspect of the present invention is an ability to access and preferably copy and store medical records 112, 114, 116 on a medical records database 110. Original medical records 112, 114, 116 would be created at each respective location by at least one of manual entry, photographic entry, electronic transfer (wired and/or wireless), dictation, and the like. The medical records 112, 114, 116 can be obtained using the Application. The medical records 112, 114, 116 can be processed using such as optical character recognition (OCR), natural language processing, graphical analysis, graphical annotations (automated annotated and/or manually annotated by a medical person), and the like. Medical records 112, 114, 116 can be obtained by electronically collecting records 113, 115, 117 entered using common practices, including manual entry, dictation, scanning computer readable images (entry of patient information, prescription information, and the like) electronically acquired data from medical equipment (X-Ray, electrocardiogram (EKG), computerized axial tomography scan (CAT Scan), Magnetic Resonance Imaging (MRI), and the like), or any other commonly recorded patient medical record information. In an enhanced option, the Application can enable a medical professional to acquire a digital image by taking a digital photograph of an image presented on a display of a medical diagnostic machine or image of notes on a computer monitor. This provides the user with an ability to capture a specific image and immediately upload the image into the patient's medical records. The image so acquired can be optimized automatically by the Application to remove artifact prior to processing and by the medical professional to clearly identify a feature of interest, which caught the attention of the medical professional. The Application can include annotation capabilities, Optical Character Recognition, Language translations, and the like to associate additional searchable information with the captured image. The Application would also automatically capture the date, time, and location of the captured image. This functionality would be provided by the feature set of the portable electronic device. The Application would enable a combination of recording methods, such as including dictation over captured images to combine notes from a medical professional in conjunction with the captured image. The Application would enable recording of the patient's description of signs of the ailment(s) to ensure accurate recording of the patient's perception and complaints. This avoids any losses in translation between the patient and any interpretations by the medical professional.

During any point in time, the medical professional can use their own human intelligence curating to parse the available data within the electronic medical records (images, recorded notes, test results, and the like) as to what is important and worth sharing/storing. This is similar to selecting the needles from the haystack.

Key contributors to diagnosing a medical condition of a patient include past history, symptoms, signs, and test data. Past history refers to past diseases diagnosed 113, 115, 117 in a patient 112, 114, 116. Symptoms refer to patient described ailments. Signs refer to information obtained during a medical examination by a medical professional. Test data refers to radiologic or laboratory data acquired by medical equipment. The history, symptoms, signs, and test data would be accessed by the Application as needed. The Application can additionally acquire electronic copies of the history, symptoms, signs, and test data information from their respective stored location(s) or electronic medical records 112, 114, 116 and maintain copies in accordance with at least one of locally (on the portable electronic device) or on a remote data storage server 110 associated with the Application. The collected data can include details of each history, symptom, sign, test data and response to treatment on a quantified scale along three categories: (a) those of severity, (b) quality and (c) time course, each scored numerically.

- a. Severity refers to the extent of disease in history ranging from mild to severe, the severity of the symptom, the size of a mass or the level of pain level in case of signs, the deviation from normal in case of lab, the size of a nodule or extent of an infiltrate in case of radiologic result and the extent of improvement in case of response to treatment.
- b. Quality refers to the type of disease in history ranging from typical to atypical, the type of pain ranging from tickling, burning, pressure, crushing in case of the symptom, the hardness of a mass or the roughness of a skin rash in case of the signs, the shape of red blood cells if describing anemia in case of the lab, the shape or calcification of a nodule or type of an infiltrate in case of radiologic result and the subjective type of improvement felt in case of response to treatment.
- c. Time refers to the duration of disease in history ranging from intermittent to chronic, the rapidity of onset of pain ranging from sudden to slow in case of the symptom, the rapidity of enlargement of the mass or skin rash in case of the signs, the rapidity of the drop in hemoglobin if describing anemia in case of the lab, rapidity of the development of an infiltrate in case of radiologic result and the rapidity of improvement felt in case of response to treatment.

These details regarding severity, quality and time regarding each factor 132, 134, 136 of a series of factors 130 can be entered manually by typing or selecting a numeric value, sliding a scale 143, 145, 147, or by using any other suitable method. The severity, quality and time course can be normalized using any suitable algorithm or any other referencing method. The numeric characterization or digitization of the data along severity, quality and time course will be customized and defined for each factor 132, 134, 136 in the Application to create consistency in data entry.

The Application can collect quantified medical data from lab test results, vital sign data and other biometric data, physical aspect tests, and any other quantified data that can be collected; then the Application can utilize the collected data to determine and present trends to the user. The presentation of the trends can be in any suitable format, including a high-low limit, an alert, a graphical representation, and the like. In extreme conditions, the process can extend an automated alert to at least one appropriate party.

In addition to obtaining data and determining trends, the Application can combine the patient's quantified data with timing of any treatment, such as delivery of medication, subjection to a medical treatment, subjection to a physical treatment, subjection to a psychological treatment, diet, and the like. This would provide a custom individualized response to a treatment association is created. The Application can enable a medical professional to theoretically adjust the timing, frequency, dosage, form, or any other contributing factor of treatment and see a predicted response (a hypothesis 170 of at least one of a diagnosis and a treatment). The hypothetical analysis can be presented in any suitable format to simplify the understanding and interpretation of the predicted results 170 by the medical professional aiding the medical professional in determining optimal treatment(s). This can include adjusting at least one treatment, which would include interactions therebetween. The analysis can optionally include genetic contributions, a micro-biome, and any other characteristics of the patient to correlate the patient's bio-genetic characteristics with the analysis.

The Application can enable the Physician or other medical professional to numerically score 143, 145, 147 the details of history, the symptoms, signs, laboratory test abnormalities and radiographic test abnormalities as well as response to treatment. The Application enables the user to annotate the patient's records, such as marking up X-Rays, Scans, etc. to convey information to other medical professionals. Different medical professionals can independently score 143, 145, 147 the symptoms, signs, laboratory and radiographic test results and response to treatment of a patient at different times. The Application can display the scoring 143, 145, 147 done by other professionals to a user to alert the other users on something they may have missed and allow them to incorporate feedback from the other medical team members. Each medical professional can use this shared information to create more accurate scoring 143, 145, 147 for his/her analysis as well as be able to learn from and be able to teach others. The medical professionals can see what information other medical professionals have entered and compare how the factors 132, 134, 136 and the detailed scoring 143, 145, 147 along the three axes which they entered affect the predicted probabilities for a given hypothesis 170. The medical professional can contact at least one other medical professional(s) to resolve any variation in agreement, particularly major disagreements in the collection and detailed scoring 143, 145, 147 of the history, symptoms, signs, tests and response to treatments (collectively subfactors 133, 135, 137). At least one of the patient, and the nurse, and any other involved party, by way of their Application, can also be involved in clarifying events in history, the symptoms, the signs, and the response to treatments in order to allow medical professionals to use more accurate data to make more accurate predictions 170 of diagnosis.

The Application additionally enables the user to numerically rank or assign values of an odds ratio 160 or a likelihood ratio to each factor 132, 134, 136 of the history, the symptoms, the signs and the response to treatment as each relates to a given hypothesis (collectively subfactors 133, 135, 137). Odds ratios 160 are numbers that can be multiplied to prior probabilities to increase or decrease the probability of that hypothesis 170 being correct. The use of odds ratios 160 can be positive if the ratio is greater than one or the ratio can be negative if the ratio is less than one. The odds ratio 160 can be entered manually by typing or selecting a numeric value, sliding a scale, or by using any other suitable method. The odds ratio 160 can be filled in automatically by the Application using the set of data built up in the system but would preferably remain editable by the doctor or other medical professional. The factors 130 (more specifically each factor 132, 134, 136) that the odds ratios 160 can be applied to, can include but would not be limited to at least one event in history, at least one symptom, at least one sign, and at least one test result as well as at least one response to at least one respective treatment (collectively subfactors 133, 135, 137). This differs from the detail scoring 143, 145, 147 of these factors along the severity, quality and time course axis as previously described herein. The Application allows visualization of all the factors 132, 134, 136, their detail scoring 143, 145, 147 along the three axis and their assigned odds ratios 160 by a medical professional to create a probability of a hypothesized diagnosis 170. The medical professional will make and enter a best guess based on at least one of experience, their knowledge of medical literature, or on any other basis, and the prevalence of each disease diagnosis hypothesis that they create. The prevalence 129 of a disease hypothesis entered by the medical professional along with the various factors 132, 134, 136 and their odds ratios 160 that affect the probability of that hypothesis 170 is used by the Application for mathematical analysis using Bayesian Statistics or Bayes theorem based or other types of calculations to output the posterior probability of that disease hypothesis. This variable, multi-factor, multi-hypothesis, analysis to apply Bayes theorem to prevalence or prior likelihoods in order to obtain the posterior or final likelihood can be repeated as each new test is done or as changes occur in existing data such that the Application shows the current probabilities for each disease hypothesis 170. The Application accounts for the correlations between the various pieces of data in the details of the severity, quality, and time course among the factors related to the history, the symptoms, the signs, the tests, and the response to the treatment. The ability of the Application to know and account for these correlations in the mathematical analysis improves (being essentially self learning) as more users enter more data regarding the various factors 132, 134, 136 found in different patients 112, 114, 116. Details of factors 132, 134, 136 that frequently occur together in a single patient are correlated and these correlations are constantly saved in the dataset. The Application can display the updated probabilities for multiple diagnoses 170 along with the prevalence criteria, the factors 132, 134, 136, the detail scores along severity, the quality and the time, and the odds ratios 160 selected by the medical professional to obtain those probabilities. In the case of multiple hypotheses 170, the conditional probabilities of having at least one hypothesis 170 or disease at the same time are also displayed. This will be visible to other medical professionals who can see and understand exactly what their colleague(s) is/are thinking. Shared visualization among a plurality of medical professionals caring for a patient will allow improvements in the hypothesis generation and be a useful teaching tool on how a combination of factors 132, 134, 136 and their relative importance 143, 145, 147 and the prevalence of a given disease can be combined to create probabilities of various hypotheses 170. The quantified scoring 143, 145, 147 of factors 132, 134, 136 by the medical professional into the Application introduces a function where the Application can use the odds ratios 160 of factors and prevalence data 129 already present in its dataset to aid in presenting at least one suggested hypothesized diagnosis and/or treatments for at least one ailment of the patient. The user can then modify the detail scoring 143, 145, 147, 149 or odds ratios 160 of at least one component and obtain updated suggested diagnosis and/or treatments for the ailment(s) of the patient. The modifications 149 to the detail scores 143, 145, 147, 149 or odds ratios 160 can be applied by manually entering a numeric value, sliding a scale, or by using any other suitable method. The changes to the detail scoring 143, 145, 147, 149 of factors 132, 134, 136 and the odds ratios 160 (respectively) can be saved to maintain a history, wherein the historical data can be retrieved and reviewed at a later point in time. For example, one medical professional can review the history of prevalence estimates 129, scoring 143, 145, 147, 149 of factors 132, 134, 136 and odds ratios 160 used by a different medical professional. The information can be presented to a user in a tabled format, a graphical format a listing format, or any other suitable format, or combination thereof.

Information can be ranked to define an importance of each element of information within the record. The ranking would enable sorting and viewing functionality. The ranking can be entered and/or sorted by the entry person (manually), an intermediary party (manually) (patient, medical professional, laboratory associate, and the like) a sending party (manually), a receiving party (manually), a classification (automated), the Application (automated), or any other suitable ranking and/or sorting process. The end result is a customized output and the level of detail with an emphasis on direction for the user at the time of review. This is to target the user's needs respective to treatment of the patient. The sorting can be further refined by increasing or decreasing a breadth of the ranking. The ranking can also direct applicability to the specific user at the time of review. For example, a pulmonary specialist would not be interested in gynecological information. The ranking can include considerations respective to a prevalence 123, 125, 127 of a history, symptom, sign, test data and/or response to a given treatment to a hypothesized diagnosis.

An increase in frequency of like validated hypothesis affirms a combination of rankings and/or odds ratios 160 of a series of prevalence, history, symptoms, signs, and test data used to generate a probability of the given hypothesis. The data set can be then presented to the medical professional to guide the medical professional in inquiring about specific prevalence 123, 125, 127, symptoms, signs, and test data. This dataset can be utilized to automatically create the odds ratios 160 for a given factor 132, 134, 136 as relates to a disease hypothesis 170. As different combinations of factors 132, 134, 136 with differing detail scoring 143, 145, 147 along severity, quality and time are validated with confirmed diagnosis, the odds ratios 160 of how each factor 132, 134, 136 changes the probability is calculated and saved. As more data are collected the accuracy of odds ratios 160 in the Application increases. The prevalence of a disease 129 in a population is also estimated more accurately by the Application as the confirmed diagnosis are saved in the dataset, such that the medical professional will no longer have to enter an estimated prevalence and an estimated the odds ratios. Medical professionals will then just enter the detail scored history, the symptoms, the signs, the tests and the response to the treatment(s) in order to automatically get a list of the disease hypothesis listed in order of probability. In effect, artificial intelligence as being applied to the medical diagnosis. The shared visualization system ensures that all changes in factors are discussed and agreed upon by the medical team caring for the patient and as those factors are changed, the disease probabilities adjust accordingly. In effect, the Applicant provides a dynamic system of collective data entry and hypothesis generation 170.

One commonly used confirmation of a diagnosis is a patient's response to treatment. In addition to acquiring the symptoms, the signs, and the test data, the Application can acquire and retain information pertaining to treatment and resulting progress of the ailment of the patient.

The Application can include a feedback system, which utilizes the obtained treatment and resulting progress of the ailment of the patient in combination with the history of factor detail scores, factor odds ratios and the associated suggested hypothesis. The feedback system enables the Application to learn a relationship between prevalence, the history, the symptoms, the signs, the test data, and response to treatment to determine at least one likely diagnosis and their probability. The feedback can also determine and suggest a recommended rate of the prevalence and the odds ratios that can be applied for the history, the symptoms, the signs, the test data, and the response to treatment based upon the dataset. The dataset can include the ailments, the treatment, and the response to treatment(s) and any other pertinent information. The Application can collect data respective to each hypothesis 170 when the respective hypothesis 170 is finalized or discarded. The Application can utilize the feedback to validate one or more hypothesis and the associated rankings of the prevalence, the symptoms, the signs, and the test data based upon the ailments, the treatment, and the response to treatment(s). The prevalence of a validated diagnosis in a given population is automatically generated in the dataset as multiple instances of that disease are encountered in the population. The relative frequencies of prevalence of one disease versus another are also automatically collected in the dataset. The process can be iterative where the medical professional or team of medical professionals would revise the factor odds ratios, prevalence's and the probabilities of the hypothesis until a final diagnosis is validated. Upon validation of the rankings, prevalence and of the hypothesis, the finalized data set would be recorded as being validated to improve the predictive capabilities of the Application in an iterative manner. Essentially, the Application is continuously learning to improve the analysis and outcome thereof.

The response to treatment can be normalized using any suitable algorithm or any other referencing method.

The Application can utilize the historical rating scales in combination with the treatment and subsequent result to learn optimization and improve the presented hypothesis 170. The feedback can provide recommended odds ratios 160 of the history, symptoms, signs, test data, and response to treatment as relates to a given disease hypothesis 170 in a patient.

The utilization of a plurality of numerical characterizations, history, symptoms, signs, laboratory and radiologic test data, response to treatment in a number of patients by various providers creates a dataset that enables the Application to determine a hypothetical relationship or correlation between each symptom, sign, laboratory and radiologic test data, and response to treatment. This correlation can be utilized in a predictive model where many diseases can be considered. Mathematical analysis of the data set is affected by the correlations between the various factors, the detail scores of the factors along severity, quality and time in the data set, the odds ratios for the factors for each disease hypothesis within the data set, the prevalence of a disease and the correlation between the factors in the dataset. Correlated findings in a given patient and a given hypothesis require specialized mathematics. The Application collects raw quantified data and determines a correlation therebetween.

In summary, the feedback portion of the Application enables self-learning to support artificial intelligence into the system based upon factual results. Because the Application has real time access to medical records, theoretical analysis, medical professional analysis, treatments, and results of many patients across a variety of regions, the Application can collect the data and improve on the artificial intelligence to optimize the recommended hypothesis or other output.

Medical records are commonly recorded by a medical professional using language or abbreviations known and understood by the medical professional creating the record. It is common place where the language or abbreviations recorded by one medical professional may differ from an understanding or interpretation by a different medical professional. This can be exasperated when dealing with medical professionals in different regions or having different primary languages.

The Application can include a translation system, wherein the Application translates the terminology recorded by one medical professional into International Classification of Diseases, class 10 (ICD-10) or any other suitable common dialect. The translation process can be referred to as Natural language processing.

Natural language processing, or any other language conversion process would be used to analyze and extract information from all of the collected medical records for each specific patient. The medical records can be collected from different physician's offices, medical treatment facilities (such as hospitals, walk in clinics, treatment facilities, etc.), independent labs, and manually entered by any individual (such as a Patient, a Physician, a Medical Assistant, and the like). The translation process converts information from different sources into a single, common format for use across any of a plurality of platforms. The common presentation format can be of any format, including text, matrix (spreadsheet), graphical, or any combination thereof. As previously mentioned, the process would preferably transcribe the records into International Classification of Diseases, class 10 (ICD-10). Conversely, the records can be converted from ICD-10 coded information into common doctor's language. The medical professional can customize their resident version of the Application by training the Application to learn the medical professional's specific terminology for converting between the medical professional's specific terminology, ICD-10, as well as other medical professional's specific terminology. The learning can be accomplished through dictation, electronic entry, corrections entered over time, or any other method. The ICD-10 can then be converted to direct, automated billing, cross transfer of diagnosis of each patient, standardizing a method of communicating between medical professionals, wherein each medical professional understands different terminology for the same medical condition/treatment/etc. and the like.

Diagnosing a medical condition of a patient requires experience. The greater or longer the experience, the higher the reliability of the diagnosis. Additionally, the better the training, the quicker the learning and the higher the reliability of the diagnosis. A primary objective of the Application is to provide an analysis system to optimize a diagnosis process based upon a collection of symptoms, lab results, analytical odds ratios, and learned results of the odds ratios.

The following provides details of the exemplary operation of the analytical portion of the Application.

Terminology

Factor=packet of information that changes odd of a diagnosis [1, 2, 3]

Subfactor=a different aspect of a factor [a, b, c] a different number of sub-factors can exist for each factor.

Numeric Values are assigned to each sub factor 1a could be 1, 2, 3, 4, 5 or 1-5 may be enough but could do visual scale in future. All sub factors will not have 1-5 division. Some may be binary yes and no.

Figure 2:
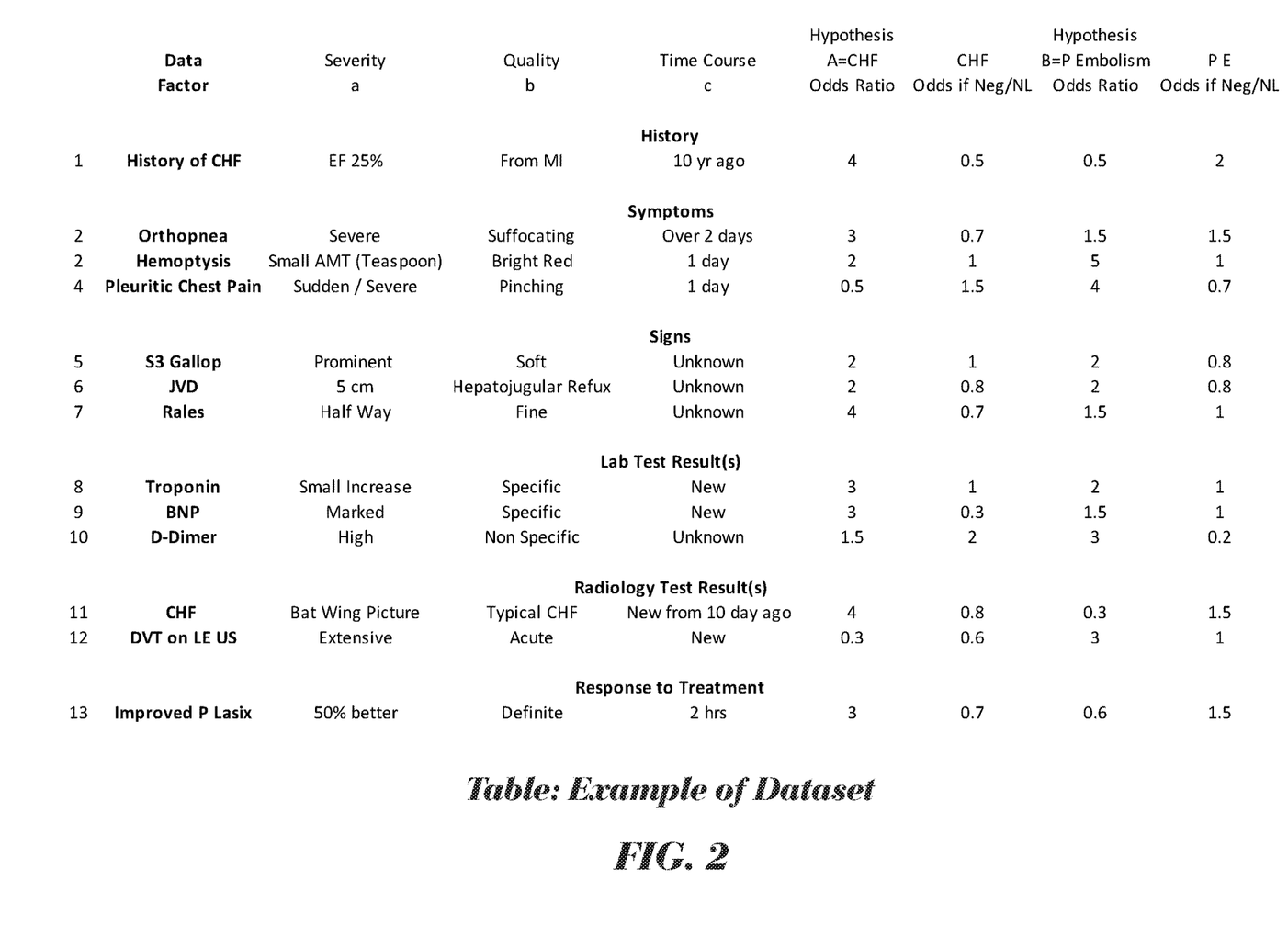
FIG. 2 presents an exemplary dataset table.

Factor 1=2a|pinchingb|3c could describe a symptom like sudden acute chest pain of severe and sharp type. This pain could be from 2 competing hypothetical diagnosis. The doctor will enter a value (1-5) for each of the diagnosis to show how much it increases or decreases the odds of that diagnosis. He may put 5 in the pulmonary embolism column and 2 in the ischemic heart disease column for this type of pain because this type of pain is seen more often in blood clot to lung than in heart attack but heart attack can sometimes have this pain too. Each combination of sub factors will have a separate odds ratio 160 for each diagnosis in the database. i.e. 1=3a|2b|1c|4d|2e may describe a different type of chest pain that will have a different chance of being associated with clots or with heart attack. Rather than have doctor put the odds on each sub factor 133, 135, 137, the doctor's brain takes in chest pain with its characteristics as a whole and places odds on it and we will do the same.

We can create a separate factor for symmetric positive and negative finding=i.e. a blood count that is high is a separate 1-5 and a low is separate 1-5 and does not have sub factors. In case of lab the 1-5 can be based on standard deviation from normal. The numeration rules for clinical sub-factors will be done by clinicians with expertise that field.

For example, when a data point, such as a white blood count (WBC) is measured, the normal WBC is between 5,000 to 12,000, the application can use a deviation from the standard to determine a weighting for the patient's condition. This can be applied in conditions where the measured WBC is below 5,000 (negative) or where the measured WBC is above 12,000 (positive).

Factors can be of different types, symptoms, signs, lab tests, imaging tests, response to treatment. We can make the factor type in the data entry but try to treat all facts the same way in the math.

Lack of a factor or absence of a symptom or sign is equally important. So no chest pain will be 1 is absent and the doctor may put 1 as a score for both the PE and chest pain. Blood clot(s) in lung and heart attack can even occur if there is no chest pain. Negative information can increase and decrease the probability of a disease. For example, if the patient lacks a symptom, the lack of the symptom would be included as a factor 132, 134, 136.

The doctor will be asked a separate question about the incidence of the diagnosis he is considering. In that hospital, and that age group, how many patient have disease x or y. Published prevalence data 123, 125, 127 could be acquired from supported sources. The published or acquired prevalence data 123, 125, 127 would be used to determine the incidence of the symptoms to aid in determining the diagnosis 170. This would be supplemental to data collected by the application and used as a method to learn predictive incidence and continuously improve the accuracy of the diagnosis 170. Maybe we could take age, demographics and socioeconomic issues and make them into factors in the future. The incidence would initially be manually entered. As the application records incidence, the application will learn and apply incidence based upon historical data.

The doctor can introduce a new factor that would be introduced into the database. The new factor would be available to other users for application of the factor. The results of the application of the new factor would be tracked to determine accuracy of the factor. As the accuracy is proven, the accuracy would be accepted or discarded accordingly.

The factors can be presented as integers, as described above, presented in fractions, or any combination thereof, alphabetically, alpha-numerically, and the like.

The factor can be adjusted by manually entering a value, referred to as a scaling factor value, sliding an indicator along a scale (either increasing or decreasing the scaling factor value), or any other suitable method of entering the data.

It is possible where one or more symptoms, or lack of a symptom, would not be characterized by a numerical value. In this instance, the software, would assign a unique identifier and apply the identifier in the mathematics to work together with other non-numerically represented and/or numerically represented symptoms to determine one or more factors that would then be included in the mathematical analysis.

An example is as follows:

Severity of shortness of breath while laying down (orthopnea) could include three subfactors, wherein two subfactors can be quantified and a third would not be quantified.

The severity could be quantified between 1-5.

The number of days can be quantified accordingly.

The quality of the orthopnea (suffocating) would not be quantified.

The combined descriptors could include two numeric values with one non-numeric value, which collectively can be used to create an odds ratio for determining the diagnosis.

Although the example presented above includes three subfactors, any number of subfactors can be included in the algorithm.

Correlations can be applied in the process. For example, a chest pain of 1=2a|pinchingb|3c type be correlated with the unilateral leg swelling of the calf because the blood clot in the leg causes the blood clot in the lung and chest pain. Both the chest pain and leg swelling will have high odds of being present in pulmonary embolism. This correlation will increase the complexity of the Bayesian analysis as the process removes the conditional independence of the factors that is required by simple Bayesian analysis. As data is collected and correlated by the application, the employment of Bayesian analysis becomes more applicable, resulting in more accurate results. Initially, the application will require the medical practitioners would be tasked with correlating the factors to suggest a diagnosis. Tracking the results will define and build a history, which will refine the correlations, thus increasing the accuracy of the output from the Bayesian analysis.

1=2a|pinchingb|3c can be deciphered as follows:
2a refers to a chest pain having a severity level of a having a numericized value of 2. ("a" refers to a severity level)
"pinchingb" refers to quality of a pinching wherein the quality of b ("b" refers to quality level)
3c refers to the time of duration; in this example referring to 3 days ("c" refers to time duration) the duration can be in other units, such as seconds, minutes, hours, days, etc. The application can include a feature to identify the associated unit of time.

The above example (1=2a|pinchingb|3c) is employed to determine an odds ratio of various diagnosis. The odds ratio would be used to determine one or more proposed diagnosis.

The idea of the system will enable users input data and later show resident doctor's system calculated odds ratios and incidence for the given information the resident doctors have entered. Restated, the process becomes a medical thinking process teaching and demonstration tool. The probabilities for a given diagnosis will be shown. At first it is a calculator: the doctor enters odds, incidence, pretest incidence. Over time, the application learns, by exposure to odds, incidence, and the like. The user can edit the odds and pretest probability. The application is thinking machine which the user interacts with and is not opaque.

The correlations between the different factors could be shown to the user. One or more screens can highlight one factor or more factors for quick identification to the user. For example, one factor can be displayed in a darker or bold font, whereas another factor can be displayed in a lighter font show the correlation with that factor and user can edit them based on the user's sense of how things work.

The application can be utilized as a training tool for resident medical practitioners. The application can record a history of the factors, correlations, prevalence assumptions, odds ratios, and the like, which resident medical practitioner entered and/or used for review by one or more senior medical practitioners. The history can be used to provide feedback to the resident medical practitioner for accuracy to provide guidance for improvements on how to determine what symptoms to look for and potential diagnosis to consider, the prevalence's of those diagnosis, what odds ratios to use, and any other insights to consider when diagnosing a patient's condition.

The application can be used as a predictive tool, whereby the user could modify one or more assumptions and see an impact on the probabilities or odds for determining a diagnosis.

As previously mentioned, the Application includes a self learning capability. The Application will continuously learn based upon historical demographics of the patient, region of the patient, symptoms of the patients, determined diagnosis of patients, proposed and applied treatments of the patients based upon the symptoms and diagnosis, and the end resolution. This process can include a determination of what prevalence and factors are to be used when suggesting a diagnosis, treatment, and the like. The learning can be optimized and continued by adjustments based upon continuous collection of the data. The system can use patient factors like the history, the symptoms, the signs, the test results and the response to treatment with a factor of prevalence of that condition in a given population. The process learns how to capture data, what data would have optimized applicability, and the like. The broadness of the Application enables collection and determination of incidence and prevalence of each disease, regionally, nationally, discretely, and the like. This can occur in real time, and be maintained through continuous updates.

The medical professionals can enter the sensitivity and specificity of each new test done on a patient based on their experience or knowledge of the literature. This can be visible and shared among medical professional and can be captured and stored in the Applications dataset. Bayesian analysis can be performed to see how the pretest probability of a disease hypothesis is changed by the test result being positive or negative, given the entered sensitivity and specificity. The value or contribution of each new test to decision making can thus be evaluated even before doing the test. If there is no significant change in the pre and post test probabilities, the test can be avoided. The medical professional can thus use the Application to help in making a decision regarding which test to do and whether to do a given test. The Application will collect data on large number of patients as to which tests are done and if the result is positive or negative and if the final diagnosis was validated. This enables the Application to create, collect and store data regarding sensitivity and specificity of a test in a given hospital or population. The sensitivity and specificity of a test can be shown to the medical professional, whereby the medical professional can use the sensitivity and specificity data to run post test probabilities on various tests. The Application can automatically run this analysis on a given set of patient information and hypothesis and suggest the next best test to do in order to make the right diagnosis. The Application thus has a self learning process where the final diagnosis and test results entered by the medical professional are used to create validated sensitivity, specificity of each test or procedure in a given setting and prevalence of that disease in a population. The Application could provide feedback to medical professionals on their usage patterns for a given test and how often it changed or did not change their post test probabilities. This feedback along with automated next best test guidance could reduce unnecessary tests and reduce costs for the medical providers, the patients, and the insurance companies.

Analysis of the medical records can be accomplished using any suitable analytical technique(s). Examples include: Bayesian Analysis and Markov Chain Monte Carlo (MCMC methods).

Bayesian Analysis is a statistical procedure which endeavors to estimate parameters of an underlying distribution based on the observed distribution. The analysis begins with a "prior distribution" which may be based on anything, including an assessment of the relative likelihoods of parameters or the results of non-Bayesian observations. In practice, it is common to assume a uniform distribution over the appropriate range of values for the prior distribution.

A theoretical joint distribution is defined as a distribution of patients interpreted in terms of their symptoms and their diseases. This joint probability distribution, when available, could be used to find the most probable disease or other medical condition associated with an observed set of symptoms. The odds ratio or likelihood is the probability of some symptom given some disease or other medical condition. The posterior probability is the probability of a disease or other medical condition given certain symptoms, signs, and the like. Though the theoretical joint distribution is unavailable, the most probable disease or other medical condition associated with an observed set of symptoms and the like can be obtained from the posterior probability distribution, which can be found using the Bayes theorem. Given the prior distribution, collect data to obtain the observed distribution. Then calculate the likelihood of the observed distribution as a function of parameter values, multiply this likelihood function by the prior distribution, and normalize to obtain a unit probability over all possible values. This is called the posterior distribution. The mode of the distribution is then the parameter estimates, and "probability intervals" (the Bayesian analog of confidence intervals) can be calculated using the standard procedure. Multiple factors can affect a posterior probability of a hypothesis and the effects of the factors can be calculated taking into account the correlations between the factors. Each new test can have a respective sensitivity and specificity applied to the pretest probability in Bayes theorem to obtain post test probabilities for at least one of a negative test and a positive test.

The prevalence of a disease or relative prevalence of diseases, the numerically characterized, quantified, or digitized detail on factors respective to the severity, the quality, and the time course, as well as an odds ratios of factors such as the history, the symptoms, the signs, the test results and the response to treatment, as well as the correlations between these factors can be used to calculate the probabilities for different hypothesis. New tests can be applied, one by one, on any hypothesis to obtain posterior or post test probabilities, which can be used to change patient management or make decisions on whether the test should be done.

The Application can keep track of the actions and the time spent by the medical professional including at least one of: entering, choosing and scoring the severity, quality and time course of the history, symptoms and signs; entering, capturing, annotating, and scoring laboratory and radiologic test data along severity, quality and time course; analyzing and entering response to treatment along severity, quality and time course; and in editing the scoring as changes in symptoms and signs and tests occur. The actions and time the medical professional takes in ranking these factors by entering or editing their odds ratios, entering hypothesis, and/or their prevalence and combining them to produce probabilities of various hypotheses can also be recorded. The actions and time the medical professional spent entering sensitivity and specificity for tests and analyzing if the test will help can also be recorded. The messaging from one medical professional to other medical professionals and the associated time spent in composing, acquiring and attaching data can also recorded. The medical professionals can enter additional time the medical professionals spend in face-to-face or phone discussions with at least one of other medical professionals and the patient's family. The Application can include links to educational material. Time spent in researching and learning about the patient's condition can be recorded as well. This data collection can support the medical professional when justifying the medical professional's billing. Rather than repeating and regurgitating the information on the chart to complete the billing process, the medical professional can take pride in doing cognitive work and justify the fees to the paying party. Markov Chain Monte Carlo methods are a class of algorithms for sampling from a probability distribution based on constructing a Markov chain that has the desired distribution as its equilibrium distribution. The state of the chain after a number of steps is then used as a sample of the desired distribution. The quality of the sample improves as a function of the number of steps. Multiple factor and variable number factor analysis can be done.

The Application enables sharing of medical records between medical professionals. Sharing of medical records enhances the overall treatment of the patient, where a diagnosis can be created by shared knowledge and hypothesis. The inclusion and utilization of the system described above to edit the number, the severity scores, the quality scores, the time course scores and the odds ratios of the factors, and edit the prevalence and the name of the hypothesis to be tested, further enhances the process, where one medical professional can import, adjust or correct their own or another medical professional's entries and potentially obtain a more accurate potential diagnosis and/or treatment. The shared or a conferencing medical review can utilize common shared charting. This process can be enhanced with the utilization of artificial intelligence. The artificial intelligence would be continuously optimizing treatment hypothesis using learned information from obtained historical patent treatment and results, and will be evaluating and recommending the right tests to make the diagnosis efficiently.

The medical professional can remind himself about the patient with a preloaded patient card and call the patient or the emergency room and give instructions to his office staff to expedite appointments.

Geo-location to optimize patient appointments and transfer of patient's files. The Application directs a transfer of the patient's medical records to the medical facility where the patient is currently located. Tagging of the patient and/or treatment location can be obtained by any known method. Additional details can be acquired and used to determine progress of treatments, etc. Patient medical records could be made inaccessible when the patient is not in the associated location. An override can be provided by a Physician to enable access when needed and when the Patient is not in the proximate area.

Geo-location can be employed to automate tracking of the Patient's care. For example, the Application can employ geo-location to determine when a patient is undergoing therapy, based upon a geographic location of the patient and a time of duration that the patient remains at that location. The Application can ensure that a patient visits a pharmacy to acquire prescription medication(s) and to see if a patient complies with the patient's dialysis schedule.

Geo-location monitoring can be employed to track compliance with appointments, track use of health facilities (such as Dialysis center appointments, urgent care center visits, health care facility appointments, rehabilitation centers appointments, home health care appointments (such as by tracking the home health care professionals), and the like). In addition to the location, the Application would include a capability for determining a length of time associated with the appointment. This can include any admission time and/or discharge time. This can also include care transition notification, which can be created and forwarded by any suitable messaging method to one or more associated medical professional, the patient, and/or the patient's family/surrogates.

In addition, the geo-location can be employed to automatically inactivate the Application when the medical professional is no longer in an active duty. The inactivation of the Application would temporarily disable the Application and delete all copies of medical records that are resident on the portable computing device to eliminate risk of exposure of the Patient's protected health information.

The Application can include a feature enabling the Patient and/or other medical professionals authorized by the patient to control which medical professionals have access and/or are denied access to the patient's protected health information.

Access to the pharmacy can verify the procurement of prescription medication(s). Geo-location processing can inform a medical professional of an arrival of a patient. Upon arriving, the Application can access the patient's medical records and have the records and any other information associated with the patient (such as messages, notes, and the like) available for the medical professional in a prioritized manner (directly presented to the medical professional) prior to and/or during the patient's appointment. The process can determine the respective medical professional by any of a number of methods, and distinguish the medical records of importance to the specific medical professional, thus only presenting the medical records of importance thereto.

The Application enables messaging between Application users. All messaging would preferably occur on a patient page in the Application to reduce risk of mistaken identity. A shared clipboard between one medical professional and other medical professionals will facilitate the pending actions for each patient.

A network effect is expected, where the primary physicians with the patient cards will help the office based medical professionals and hospital based medical professionals with timesaving information and the various medical professionals in return will share their recommendations, hospital events and discharge plan with the primary doctors or other office based medical professionals. Patients can see who their office based medical professionals and hospital based medical professionals are and be able to see and get appointment reminders for all of the patient's office based medical professionals. The patients will control their physician's list and the medical professional's access to their information. The Application includes innovative messaging features unique to healthcare needs to allow multiple caregivers to communicate intelligently with one another. Increased efficiency of office visits, timely communication among doctors and shared critical outpatient and inpatient information will reduce duplication, improve coordination and reduce admissions.

The Application enables a feature referred to herein as message clustering. Message clustering combines like messages or other information related to a specific interest, such as symptoms, signs, a diagnosis, a patient, a treatment, a geographic relation, and the like. The information would preferably be provided to the medical professional at a time period associated with an event, such as a patient appointment, a patient review, and the like.

The messaging can be configured to enable function based or level based messaging.

More specifically, a message that is more appropriate for a physician would be directed to the physician, whereas a message for an appointment would be directed to the receptionist for the physician. The user would select a desired group to receive the message and the Application would determine the optimal recipient from the group of recipients associated with the desired group based upon the intentions of the message and the established function associated with the party within the group.

The Application can include a feature to automatically trigger a conveyance of educational information, instructions, guidelines, potential side effects, diagnosis related expectations, or any other information to the patient and/or other medical professionals. The information can be presented in any suitable format, including text, graphical images, photographs, video, audio, and the like.

It is understood that the Application can include any of the above described features, a plurality of the above described features, or all of the above described features. The Application can be enhanced including any other known or newly conceived feature without limiting the present invention. The Application can be adapted to new platforms as hardware is developed and technology advances.

Sequential Tests: Choosing the Next and the Best Sequence of Tests

Physicians use published sensitivity and specificity of a test in decision making assuming that the sensitivity and specificity of a test are constant among patient populations. They assume that the conditional probability of a test result is independent of the prior probability of the disease. In the proposed system, the system will create posterior probabilities for the given hypothesis as each piece of data is added. The posterior probability generated for a given hypothesis after applying any new information will then be used sequentially in Bayesian analysis as the prior probability for the next test. Applying this technique to complete the various tests in different orders will allow the Application to determine an optimal recommended sequence for administering the various proposed tests.

When using Bayes theorem to interpret a sequence of tests, it is assumed that the tests are conditionally independent of one another. Being conditionally independent means that the order in which the tests are done does not affect the tests sensitivity and specificity. Since the system will have large number of patients with similar pretest likelihoods who have at least two tests in various sequences, any conditional dependence effect will become apparent and the appropriate level of sensitivity and specificity can be applied based upon the sequence of tests utilized. The level of sensitivity and/or specificity would be automatically optimized by repetition of the use of the Application and feedback of the results. Additionally, automatic Application of corrective factors for conditional dependents can further optimize the level of sensitivity and/or specificity. The will lead to improvements pertaining to the order of administration of each respective proposed test. This will lead to improved accuracy in predicting probability of one or more given diseases or other medical conditions.

The tests are evaluated in studies that have populations different from the population that the test is applied in. The spectrum bias is eliminated if the treatment population is the same population as the one that provides the test characteristics like sensitivity and specificity. The doctor or other medical professional will know how the given test administered to the patient in the medical facility and using the available machines performs because the Application stores aggregated data collected over time. The receiver operating characteristic of a given test can be constructed and the system can use the exact sensitivity and specificity for a given value of attest rather than just the positive or negative result of attest based on an arbitrary cutoff. The receiver operating characteristic provides the user with best manner to convey a value of a test for any given condition.

The best sequence and combination of tests can be suggested based on the pretest probability at that time for that patient in that population.

Shared Decision Making

Shared decision making is considered to be one of the six pillars of high quality care according to the institute of medicine. The disclosed Application could provide educational links to various appropriate websites. For example, the Application could forward the patient to www.Patient-decisionaid.org to help the patient decide whether to get an Implantable Converter Defibrillator or not, or whether the patient should be on blood thinners for atrial fibrillation, or not. These decisions depend upon evidence-based guidelines as well as patient values and preferences. The patient may make a decision which is not the best decision based on population based guidelines, but the best decision for them based on the patient's understanding of the treatment effect, the patient's quality of life, and the number needed to treat to get the desired effect. The patient can get input from all of the patient's doctors regarding important medical decision.

Decision Making

Customized Decision trees can be constructed based on existing patient factors and a variable sequence of future tests that can be administered utilizing the data in the system. Each test result will define a node leading to further branching options and ending in a result such as cure, different types of disability, and different times of death. Probabilistic analysis and folding back analysis of the decision trees can then compute the probability of a given outcome. The patient and the doctor or other suitable medical professional can use the patient's risk tolerance and expected value of different options to choose the patient's preferred outcome and then be guided to the next step that moves the patient towards their desired outcome. This will have an effect of simplifying and visualizing a complex clinical decision making process.

Similarly a more complex analysis can be completed that takes the time between events into account using Markov models instead of decision trees. Monte Carlo simulations can be run to randomly generate a large sample of possible paths though the Markov model to predict an effect of interventions, such as smoking cessation, administration of any given treatment, and the like on a quality of life and/or life expectancy for a given patient.

Shared Decision Making Among Doctors

Doctors can subjectively assess a ratio between potential harm and expected benefit respective to a treatment and the system will use that to provide the threshold probability where that doctor should decide to treat. $[p=(H/B)/(1+H/B)]$ The patient can be involved in guiding the doctor to the correct Harms and Benefits probabilities by entering their preferences or utilities for the disease treatment states. The patient and his doctors can visualize the patient preferences, estimate harms and benefits, calculate treatment threshold probabilities and then use the predicted probabilities to decide the next treatment option. This customized approach will provide better treatment than guideline based cookbook medicine.

What is claimed is:

1. A method for developing and utilizing artificial intelligence to determine a suggested hypothesis of at least one of a diagnosis and a treatment using an application operating on a portable computing device, the method comprising steps of:
   accessing the portable computing device, the computing device comprising the artificial intelligence utilizing a microprocessor in digital communication with a digital data storage device;
   developing the artificial intelligence using the following steps: establishing and maintaining a database of a plurality of patients' electronic medical records on the digital storage device;
   entering a series of subfactors into the portable computing device, wherein the subfactors are entered in a quantified format, collectively the subfactors define a factor;
   storing the series of quantified subfactors in a patient's electronic medical records on a medical records data server; introducing a scoring factor that adjusts an importance of each factor; adjusting each factor based upon the scoring factor using the microprocessor;
   calculating an odds ratio for each of the factors associated with a current medical condition of the patient based upon the stored patient's electronic medical records, wherein the step of calculating the odds ratio is accomplished using the microprocessor;
   calculating a prevalence of diagnoses based upon a frequency of previously determined diagnoses associated with other patients having like symptoms within the database of patients' electronic medical records, wherein the step of calculating the prevalence of diagnoses is accomplished using the microprocessor; and
   determining the suggested hypotheses of the at least one of the diagnoses and the treatment based upon the odds ratios of the factors associated with the health condition affecting multiple possible hypotheses of possible diagnoses of the current medical condition of the patient and a possible treatment of the current medical condition of the patient within the patient's electronic medical records, wherein the step of determining the hypotheses is accomplished by the microprocessor;
   adjusting each scoring factor based upon a comparison between an actual result and the suggested hypotheses of the at least one of the diagnoses and the treatment, wherein the adjusting of each scoring factor is established by a first medical professional, creating a first set of scoring factors using the portable computing device;
   storing a record comprising the first set of scoring factors and resulting hypotheses for reference; and
   repeating the step of adjusting each scoring factor, wherein the repeated step is accomplished by scoring factors is established by each subsequent medical professional via the application over a network, creating a subsequent set of scoring factors established by each subsequent medical professional,
   wherein the results created by each subsequent set of scoring factors and results created by first set of scoring factors are provided for comparison between results by medical professionals,
   wherein a history of the results are utilized as a contributor to an artificial intelligence component used by the microprocessor to determine improved suggested hypotheses of the at least one of the diagnoses and the treatment,
   wherein each of the first medical professional and the subsequent medical professional are establishing the respective set of scoring factors using different portable computing devices while in different locations,
   obtaining medical records, including symptoms, from a subject patient for diagnosis of a medical condition,
   utilizing the artificial intelligence learned by information obtained from historical patient medical records, diagnosis, treatment, and results to make the diagnosis of the medical condition of the subject patient efficiently, wherein the artificial intelligence utilizes an iterative process based upon the symptoms included in the obtained medical records of the subject patient and the obtained historical patient diagnosis, treatment, and results.

2. The method as recited in claim 1, wherein the subfactors can include at least one of: severity scores, quality scores, time course scores and response to treatment scores.

3. The method as recited in claim 1, further comprising steps of:
   adjusting the quantified subfactors in the patient's electronic medical records to determine if the adjustment of the quantified subfactors affects the suggested hypotheses of the at least one of the diagnoses and the treatment.

4. The method as recited in claim 1, further comprising steps of:
  adjusting the odds ratios based upon the factors associated with a health condition within the stored patient's electronic medical records to determine if the adjustment of the odds ratios affects the suggested hypotheses of the at least one of the diagnoses and the treatment.

5. The method as recited in claim 1, wherein the prevalence can be based upon at least one of: location, age, ethnicity, gender, genetic makeup, environmental exposures, family history, environmental clustering, geographic clustering, incidence of a given condition, incidence of a given condition in a geographic region, and recent patient travel history.

6. The method as recited in claim 1, further comprising steps of:
  entering a final diagnosis respective to the suggested hypotheses of the at least one of the diagnoses and the treatment based upon the odds ratios and prevalence;
  establishing a correlation between the final diagnosis and the suggested hypotheses of the at least one of the diagnoses and the treatment based upon the odds ratios and prevalence, using the correlation between the final diagnosis and the suggested hypotheses of the at least one of the diagnoses and the treatment based upon the odds ratios to improve the step of determining the odds ratios and prevalence.

7. The method as recited in claim 1, wherein the factors can include at least one of: symptoms, signs, lab tests, imaging tests, and response to treatment.

8. The method as recited in claim 1, further comprising a step of:
  employing correlations between at least one of a numerical characterization of the factors, a quantified characterization of the factors, and digitized detail of the factors respective to at least one of a severity, a quality, a time course, and the odds ratio of factors to calculate probabilities of different hypotheses.

9. A method for developing and utilizing artificial intelligence to determine a suggested hypotheses of at least one of a diagnosis and a treatment using an application operating on a portable computing device, the method comprising steps of:
  accessing the portable computing device, the computing device comprising the artificial intelligence utilizing a microprocessor in digital communication with a digital data storage device;
  establishing and maintaining a database of a plurality of patients' electronic medical records on the digital storage device;
  entering a series of subfactors into the portable computing device, wherein the subfactors are entered in a quantified format, collectively the subfactors define a factor;
  storing the series of quantified subfactors in a patient's electronic medical records on a medical records data server;
  introducing a scoring factor that adjusts an importance of each factor;
  adjusting each factor based upon the scoring factor using the microprocessor;
  calculating an odds ratio for each of the factors associated with a current medical condition of the patient based upon the stored patient's electronic medical records, wherein the step of calculating the odds ratio is accomplished using the microprocessor;
  calculating a prevalence of diagnoses based upon a frequency of previously determined diagnoses associated with other patients having like symptoms within the database of patients' electronic medical records, wherein the step of calculating the prevalence of diagnoses is accomplished using the microprocessor;
  determining a suggested hypothesis of the at least one of the diagnosis and the treatment by forming a posterior probability distribution using the odds ratios of the factors associated with a health condition and the prevalence of the health conditions, wherein the step of determining the suggested hypothesis is accomplished by the microprocessor;
  adjusting each scoring factor based upon a comparison between an actual result and the suggested hypothesis of the at least one of the diagnosis and the treatment, wherein the adjusting of each scoring factor is established by a first medical professional, creating a first set of scoring factors using the portable computing device;
  storing a record comprising the first set of scoring factors and resulting hypotheses for reference; and
  repeating the step of adjusting each scoring factor, wherein the repeated step is accomplished by scoring factors is established by each subsequent medical professional via the application over a network, creating a subsequent set of scoring factors established by each subsequent medical professional,
  wherein the results created by each subsequent set of scoring factors and results created by first set of scoring factors are provided for comparison between results by medical professionals,
  wherein a history of the results are utilized as a contributor to an artificial intelligence component used by the microprocessor to determine improved suggested hypotheses of the at least one of the diagnoses and the treatment,
  wherein each of the first medical professional and the subsequent medical professional are establishing the respective set of scoring factors using different portable computing devices while in different locations;
  obtaining medical records, including symptoms, from a subject patient for diagnosis of a medical condition,
  utilizing the artificial intelligence learned by information obtained from historical patient medical records, diagnosis, treatment, and results to make the diagnosis of the medical condition of the subject patient efficiently, wherein the artificial intelligence utilizes an iterative process based upon the symptoms included in the obtained medical records of the subject patient and the obtained historical patient diagnosis, treatment, and results.

10. The method as recited in claim 9, wherein the step of forming the posterior probability distribution is accomplished using Bayesian statistics.

11. The method as recited in claim 9, further comprising steps of:
  entering a final diagnosis respective to the suggested hypothesis of the at least one of the diagnosis and the treatment based upon the odds ratios and prevalence;
  establishing a correlation between the final diagnosis and the suggested hypothesis of the at least one of the diagnosis and the treatment based upon the odds ratios and prevalence, using the correlation between the final diagnosis and the suggested hypothesis of the at least one of the diagnosis and the treatment based upon the odds ratios to improve the step of determining the odds ratios and prevalence.

12. The method as recited in claim 9, wherein the posterior probability distribution calculates a likelihood of an observed distribution as a function of parameter values; multiplies a likelihood function by a prior distribution, and normalizes the likelihood function to obtain a unit probability over all possible values.

13. The method as recited in claim 9, wherein the posterior probability distribution is determined using Bayesian statistics, the method further comprising a step of: including a respective sensitivity and specificity applied to a pretest probability in Bayesian statistics to obtain post test probabilities for at least one of a negative test and a positive test for each new test.

14. The method as recited in claim 9, wherein the subfactors can include at least one of: severity scores, quality scores, time course scores and response to treatment scores.

15. The method as recited in claim 9, further comprising steps of:
adjusting the quantified subfactors in the patient's electronic medical records to determine if the adjustment of the quantified subfactors affects the suggested hypothesis of the at least one of the diagnosis and the treatment.

16. The method as recited in claim 9, further comprising a step of:
learning to increase accuracy of each subsequently suggested hypothesis of the at least one of the diagnosis and the treatment by employing correlations with considerations which include at least one of: posterior probability distribution, subfactors, factors, odds ratios, prior prevalence of the health conditions, and collected data.

17. The method as recited in claim 9, further comprising a step of:
applying at least one of Markov models and Monte Carlo simulations to further enhance the step of determining the hypothesis of the at least one of the diagnosis and the treatment, wherein the at least one of Markov models and Monte Carlo simulations are accomplished by the microprocessor.

18. A method for developing and utilizing artificial intelligence to determine a suggested hypotheses of at least one of a diagnosis and a treatment using an application operating on a portable computing device, the method comprising steps of:
accessing the portable computing device, the computing device comprising the artificial intelligence utilizing a microprocessor in digital communication with a digital data storage device;
establishing and maintaining a database of a plurality of patients' electronic medical records on the digital storage device;
entering a series of subfactors into the portable computing device, wherein the subfactors are entered in a quantified format, collectively the subfactors define a factor;
storing the series of quantified subfactors in a patient's electronic medical records on a medical records data server;
introducing a scoring factor that adjusts an importance of each factor;
adjusting each factor based upon the scoring factor using the microprocessor;
calculating an odds ratio for each of the factors associated with a current medical condition of the patient based upon the stored patient's electronic medical records, wherein the step of calculating the odds ratio is accomplished using the microprocessor;
calculating a prevalence of diagnoses based upon a frequency of previously determined diagnoses associated with other patients having like symptoms within the database of patients' electronic medical records, wherein the step of calculating the prevalence of diagnoses is accomplished using the microprocessor;
determining a suggested hypothesis of the at least one of the diagnosis and the treatment based upon the odds ratios of the factors associated with the health condition affecting multiple possible hypotheses of a possible diagnosis and a possible treatments within the patient's electronic medical records, wherein the step of determining the hypothesis is accomplished by the microprocessor;
determining a next medical investigation based upon a respective sensitivity and specificity wherein the step of determining the next medical investigation is accomplished by the microprocessor; and
adjusting each scoring factor based upon a comparison between an actual result and the suggested hypothesis of the at least one of the diagnosis and the treatment, wherein the adjusting of each scoring factor is established by a first medical professional, creating a first set of scoring factors using the portable computing device;
storing a record comprising the first set of scoring factors and resulting hypotheses for reference; and
repeating the step of adjusting each scoring factor, wherein the repeated step is accomplished by scoring factors is established by each subsequent medical professional via the application over a network, creating a subsequent set of scoring factors established by each subsequent medical professional,
wherein the results created by each subsequent set of scoring factors and results created by first set of scoring factors are provided for comparison between results by medical professionals,
wherein a history of the results are utilized as a contributor to an artificial intelligence component used by the microprocessor to determine improved suggested hypotheses of the at least one of the diagnoses and the treatment,
wherein each of the first medical professional and the subsequent medical professional are establishing the respective set of scoring factors using different portable computing devices while in different locations;
obtaining medical records, including symptoms, from a subject patient for diagnosis of a medical condition,
utilizing the artificial intelligence learned by information obtained from historical patient medical records, diagnosis, treatment, and results to make the diagnosis of the medical condition of the subject patient efficiently, wherein the artificial intelligence utilizes an iterative process based upon the symptoms included in the obtained medical records of the subject patient and the obtained historical patient diagnosis, treatment, and results.

19. The method as recited in claim 18, further comprising a step of: determining a plurality of next medical investigations based upon the respective sensitivity and specificity.

20. The method as recited in claim 18, further comprising a step of: determining a plurality and order of next medical investigations based upon the respective sensitivity and specificity.

* * * * *